United States Patent
Hardert et al.

(10) Patent No.: US 8,951,218 B2
(45) Date of Patent: Feb. 10, 2015

(54) MULTI-PATH CATHETER

(75) Inventors: Michael Hardert, Bloomington, IN (US); Michael Robert Kurrus, Ellettsville, IN (US); Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 231 days.

(21) Appl. No.: 13/412,064

(22) Filed: Mar. 5, 2012

(65) Prior Publication Data

US 2012/0232470 A1 Sep. 13, 2012

Related U.S. Application Data

(60) Provisional application No. 61/450,854, filed on Mar. 9, 2011.

(51) Int. Cl.
*A61M 37/00* (2006.01)
*A61M 25/00* (2006.01)

(52) U.S. Cl.
CPC ....... *A61M 25/0032* (2013.01); *A61M 25/0026* (2013.01); *A61M 2025/0031* (2013.01); *A61M 2025/0034* (2013.01)
USPC ........................................ 604/4.01; 604/6.16

(58) Field of Classification Search
CPC .................... A61M 25/0026; A61M 25/0032; A61M 2025/0031; A61M 2025/0034
USPC ......... 604/4.01, 5.01, 6.16, 27–30, 35, 39–45
See application file for complete search history.

(56) References Cited

U.S. PATENT DOCUMENTS

| | | |
|---|---|---|
| 4,995,865 A | 2/1991 | Gahara et al. |
| 5,451,206 A | 9/1995 | Young |
| 6,001,079 A | 12/1999 | Pourchez |
| 6,074,374 A | 6/2000 | Fulton |
| 6,190,349 B1 | 2/2001 | Ash et al. |

(Continued)

FOREIGN PATENT DOCUMENTS

EP 332366 A2 * 9/1989

OTHER PUBLICATIONS

Stephen R. Ash; Advances in Tunneled Central Venous Catheters for Dialysis: Design and Performance; Reducing Tunneled Hemodialysis Catheter Morbidity; 2008; pp. 1-12; Wiley Periodicals, Inc.

(Continued)

*Primary Examiner* — Theodore Stigell
(74) *Attorney, Agent, or Firm* — Liell + McNeil

(57) ABSTRACT

A multi-path catheter includes an elongate tubular member and a withdrawal pathway along which unfiltered fluid is withdrawn in a distal to proximal direction. The withdrawal pathway originates at a distal point and is at least partially defined by the elongate tubular member. The elongate tubular member also defines, at least partially, at least one infusion pathway along which filtered fluid is returned in a proximal to distal direction. The at least one infusion pathway extends distally beyond the withdrawal pathway. First and second legs of the elongate tubular member are positioned on opposing sides of the withdrawal pathway at the distal point, and the at least one infusion pathway is at least partially defined by one of the first and second legs. The first and second legs have outer walls that are unattached to one another at distal ends thereof.

20 Claims, 4 Drawing Sheets

(56) References Cited

U.S. PATENT DOCUMENTS

| | | |
|---|---|---|
| 6,409,700 B1 | 6/2002 | Siegel, Jr. et al. |
| 6,461,321 B1 | 10/2002 | Quinn |
| 6,695,832 B2 | 2/2004 | Schon et al. |
| 6,808,510 B1 | 10/2004 | DiFiore |
| 6,881,211 B2 | 4/2005 | Schweikert et al. |
| 6,966,886 B2 | 11/2005 | Appling |
| 7,108,674 B2 | 9/2006 | Quinn |
| 7,141,035 B2 | 11/2006 | Haggstrom |
| RE39,451 E | 12/2006 | Kuhle |
| 7,322,953 B2 | 1/2008 | Redinger |
| 7,776,005 B2 | 8/2010 | Haggstrom et al. |
| 2005/0261663 A1 | 11/2005 | Patterson et al. |
| 2008/0097382 A1 | 4/2008 | McGuckin, Jr. et al. |
| 2008/0214980 A1* | 9/2008 | Anand .................. 604/6.16 |
| 2009/0205189 A1* | 8/2009 | Nimkar et al. ............ 29/460 |
| 2009/0312687 A1 | 12/2009 | DeFonzo et al. |
| 2010/0191165 A1* | 7/2010 | Appling et al. .......... 604/6.16 |

OTHER PUBLICATIONS

Angiodynamics Incorporated; High Performance Engineering. Dynamic Flow Chronic Hemodialysis Catheter; pp. 1-4.

Split Cath III; Split Cath III with TriniFlex Material; www.medcompnet.com; pp. 1-2.

Arrow Edge; Antegrade-Tunneled Chronic Hemodialysis Catheter; pp. 1-4.

Michael G. Tal, MD, MBA and Nina Ni, AB; Selecting Optimal Hemodialysis Catheters: Material, Design, Advanced Features, and Preferences; Yale University School of Medicine, New Haven, CT, USA; pp. 1-6.

* cited by examiner

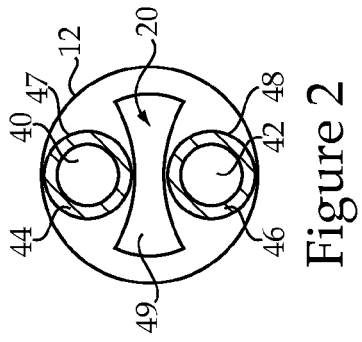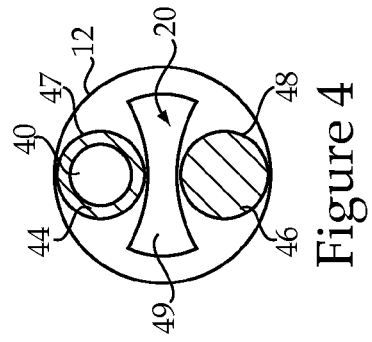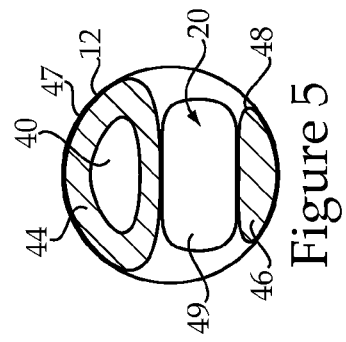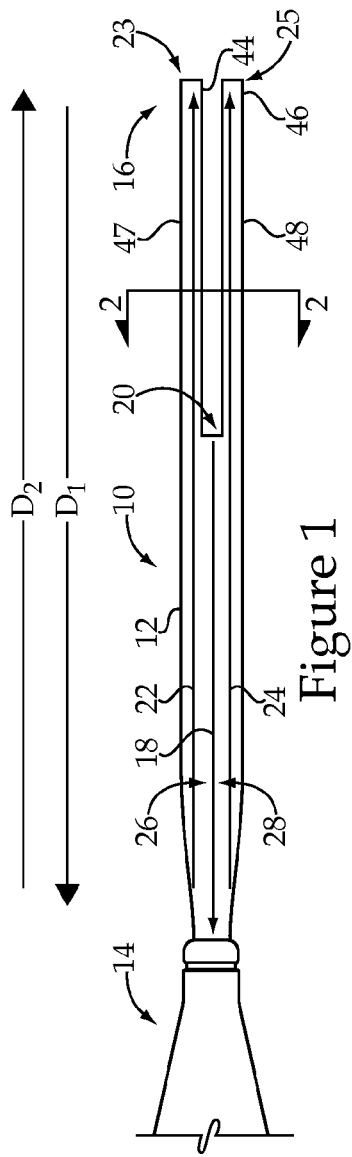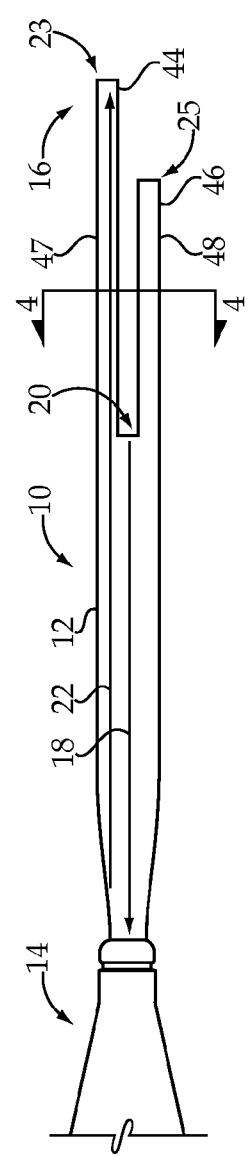

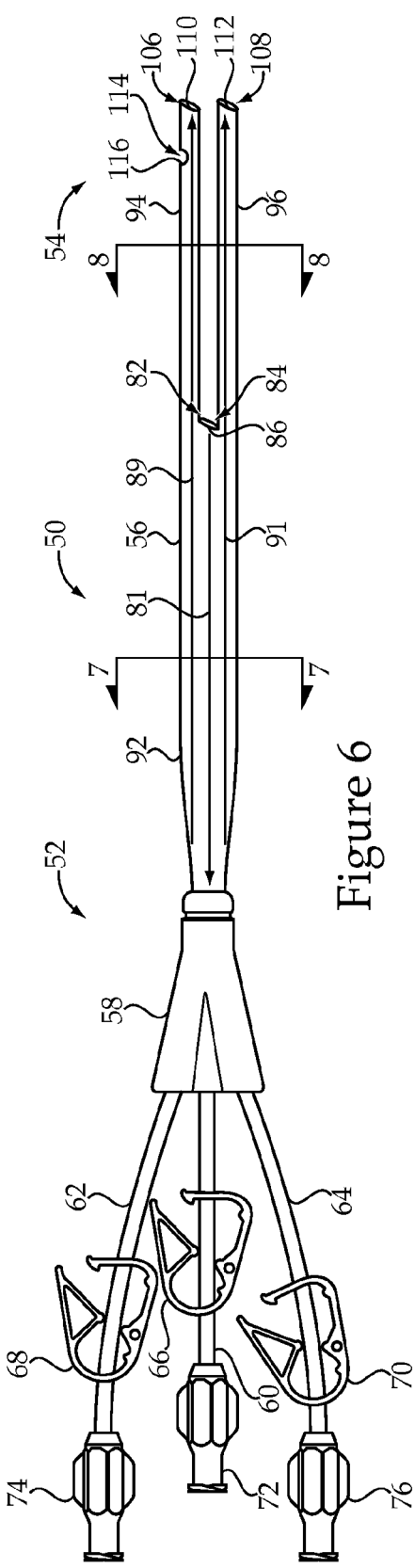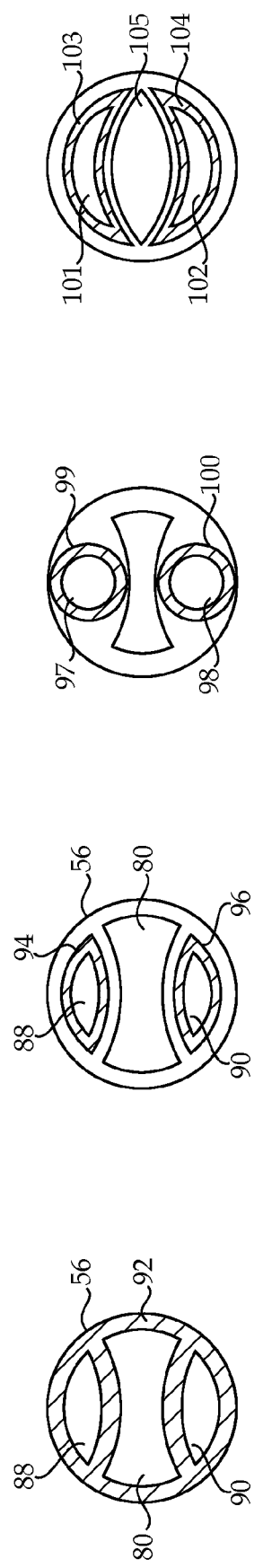

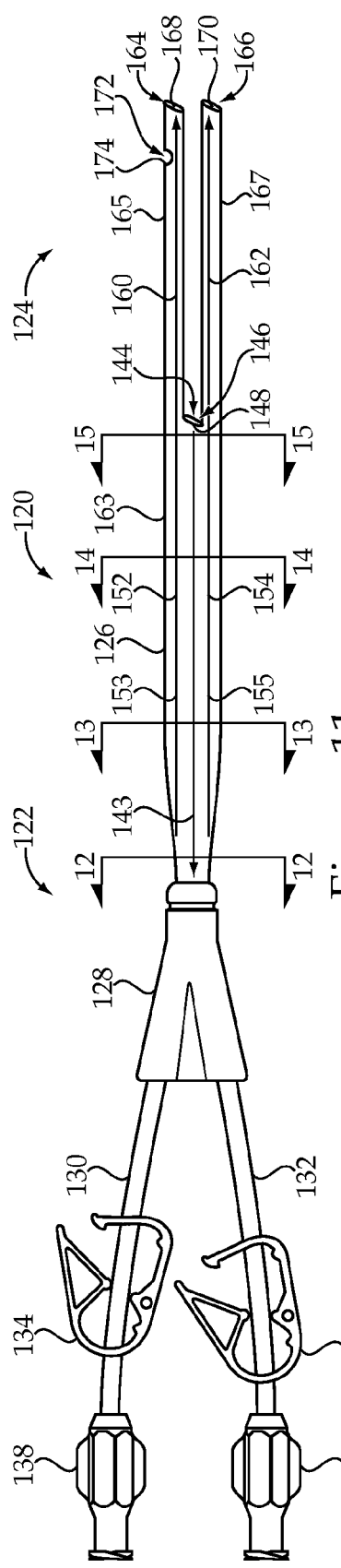
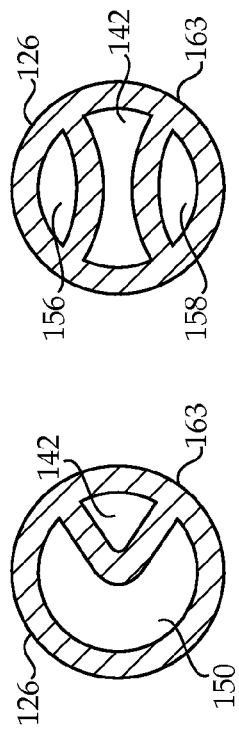
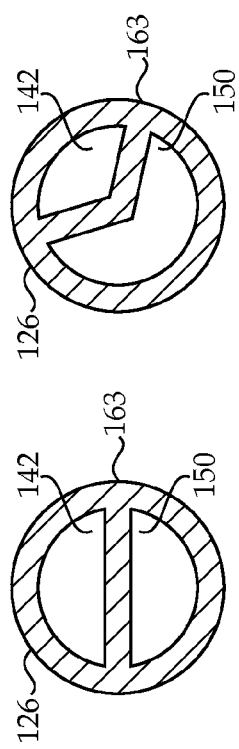
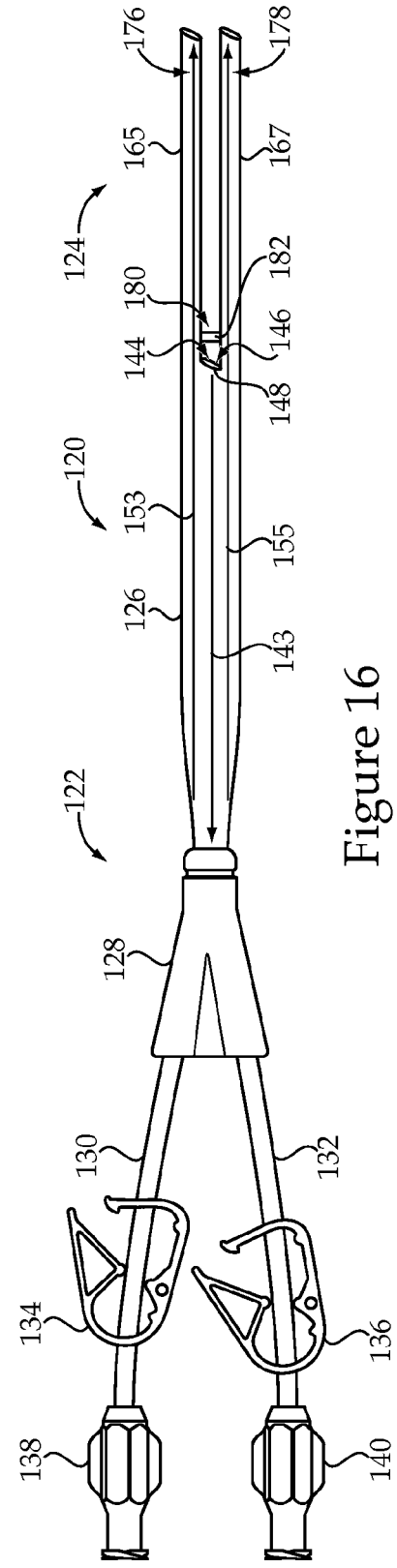
Figure 11
Figure 12
Figure 13
Figure 14
Figure 15
Figure 16

MULTI-PATH CATHETER

RELATION TO OTHER PATENT APPLICATION

This application claims priority to provisional patent application 61/450,854, filed Mar. 9, 2011 with the same title.

TECHNICAL FIELD

The present disclosure relates generally to the field of vascular intervention, and more particularly to a multi-path catheter for withdrawing bodily fluids from a patient vessel for treatment and returning the treated bodily fluids to the patient vessel.

BACKGROUND

Dual lumen catheters are commonly used in the field of vascular intervention and, more particularly, are used in extracorporeal treatment procedures of bodily fluids. For example, a bodily fluid may be withdrawn from a patient vessel through one lumen of a dual lumen catheter, subjected to a treatment process, and then returned to the patient vessel through the other lumen of the dual lumen catheter. One such extracorporeal treatment process that often utilizes a dual lumen catheter is hemodialysis. During a hemodialysis procedure, blood is withdrawn from a blood vessel through a withdrawal lumen of the catheter and routed through a dialysis machine, such as a dialyzer, where waste products are removed from the blood. The cleansed, or filtered, blood is then returned to the blood vessel through an infusion lumen of the catheter.

A dual lumen catheter, when used for hemodialysis, is generally inserted into the patient through the jugular vein, subclavian vein, or the femoral vein. Although a dual lumen catheter is typically used for temporary vascular access, it may be used for long-term access while a permanent access, such as a fistula, develops, or in situations where a permanent access is not feasible. If long-term catheter use is necessary, the catheter may be tunneled under the skin to increase comfort for the patient and reduce complications.

Common dual lumen catheters used in hemodialysis procedures are referred to as split tip catheters, having staggered lumens, where one lumen, typically the infusion lumen, terminates distal to the other lumen, typically the withdrawal lumen. Some problems exhibited with the use of these split tip catheters include the withdrawal lumen "sucking" against the vessel wall. Specifically, a distal tip, or port, of the withdrawal lumen may suction against the vessel wall, leaving the withdrawal lumen partially or completely occluded by the patient's vasculature. An addition problem related to dual lumen catheters includes the recirculation of cleansed blood, which may lower the efficiency of the hemodialysis procedure.

The present disclosure is directed toward one or more of the problems set forth above.

SUMMARY OF THE DISCLOSURE

In one aspect, a multi-path catheter includes an elongate tubular member and a withdrawal pathway along which unfiltered fluid is withdrawn in a distal to proximal direction. The withdrawal pathway originates at a distal point and is at least partially defined by the elongate tubular member. The elongate tubular member also defines, at least partially, at least one infusion pathway along which filtered fluid is returned in a proximal to distal direction. The at least one infusion pathway extends distally beyond the withdrawal pathway. First and second legs of the elongate tubular member are positioned on opposing sides of the withdrawal pathway at the distal point, and the at least one infusion pathway is at least partially defined by one of the first and second legs. The first and second legs have outer walls that are unattached to one another at distal ends thereof.

In another aspect, a method of performing a hemodialysis procedure on a patient using a multi-path catheter includes a step of directing a filtered fluid into a vessel of the patient along at least one infusion lumen, wherein the at least one infusion lumen is at least partially defined by one of the first and second legs. The method also includes inhibiting blockage of a withdrawal pathway, at least in part, by flanking a distal point of the withdrawal pathway with first and second legs, and inhibiting fluid recirculation, at least in part, by spacing a distal point of the at least one infusion pathway a predetermined distance from the distal point of the withdrawal pathway.

BRIEF DESCRIPTION OF THE DRAWINGS

FIG. 1 is a side diagrammatic view of a portion of a multi-path catheter according to the present disclosure;

FIG. 2 is a cross sectional view of the multi-path catheter of FIG. 1 taken along lines 2-2 according to the present disclosure;

FIG. 3 is a side diagrammatic view of a portion of an alternative multi-path catheter according to the present disclosure;

FIG. 4 is a cross sectional view of the multi-path catheter of FIG. 3 taken along lines 4-4 according to the present disclosure;

FIG. 5 is an alternative cross sectional view of the multi-path catheter of FIG. 3 taken along lines 4-4 according to the present disclosure;

FIG. 6 is a perspective view of a multi-path catheter according to a specific embodiment of the present disclosure;

FIG. 7 is a cross sectional view of the multi-path catheter of FIG. 6 taken along lines 7-7 according to the present disclosure;

FIG. 8 is a cross sectional view of the multi-path catheter of FIG. 6 taken along lines 8-8 according to the present disclosure;

FIG. 9 is an alternative cross sectional view of the multi-path catheter of FIG. 6 taken along lines 8-8 according to the present disclosure;

FIG. 10 is another alternative cross sectional view of the multi-path catheter of FIG. 6 taken along lines 8-8 according to the present disclosure;

FIG. 11 is a perspective view of a multi-path catheter according to another specific embodiment of the present disclosure;

FIG. 12 is a cross sectional view of the multi-path catheter of FIG. 11 taken along lines 12-12 according to the present disclosure;

FIG. 13 is a cross sectional view of the multi-path catheter of FIG. 11 taken along lines 13-13 according to the present disclosure;

FIG. 14 is a cross sectional view of the multi-path catheter of FIG. 11 taken along lines 14-14 according to the present disclosure;

FIG. 15 is a cross sectional view of the multi-path catheter of FIG. 11 taken along lines 15-15 according to the present disclosure;

FIG. 16 is a perspective view of the multi-path catheter of FIG. 11 including a collapse inhibiting member according to the present disclosure.

DETAILED DESCRIPTION

Figure 17:
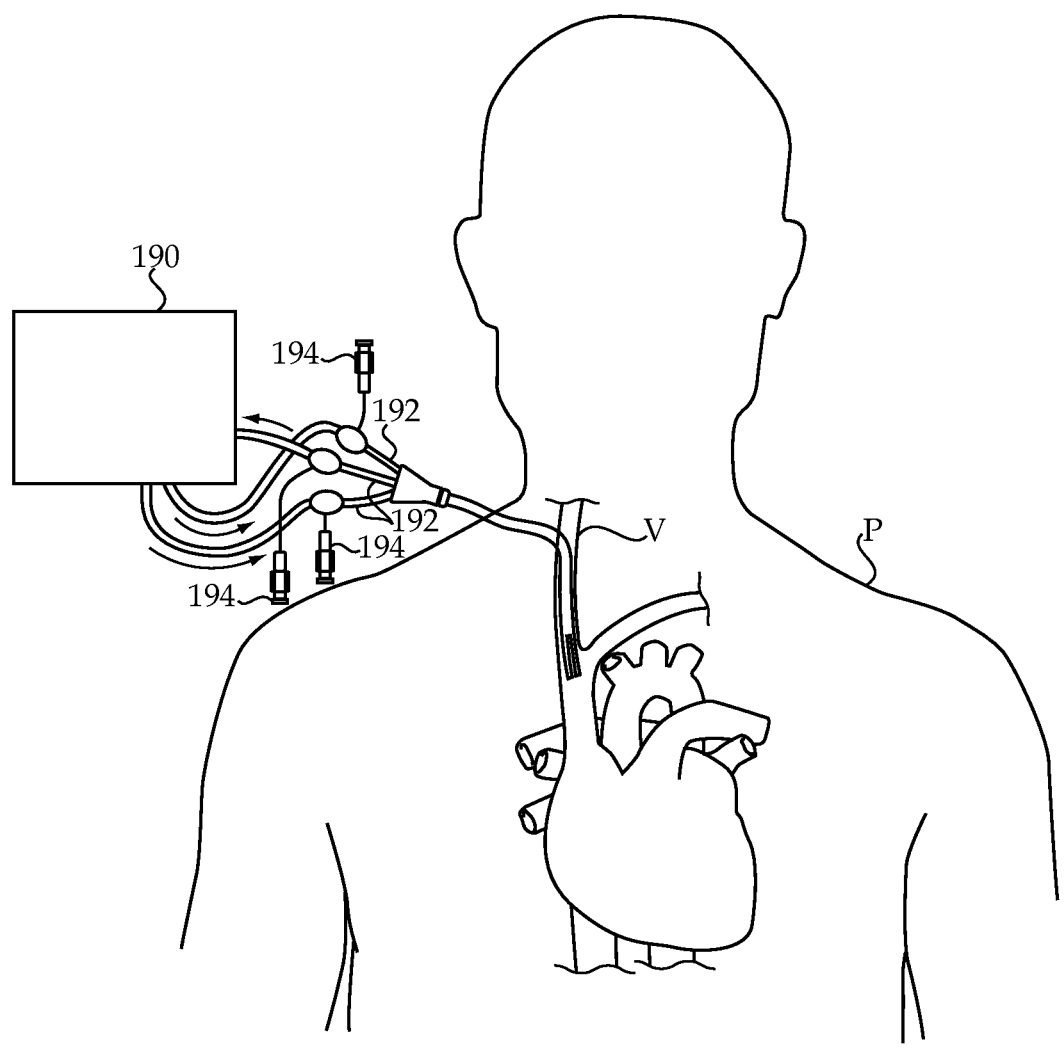
FIG. 17 is a diagrammatic view of a stage of a hemodialysis procedure, according to one aspect of the present disclosure.

Referring to FIG. 1, there is shown a portion of a multi-path catheter 10 according to the present disclosure. Although the multi-path catheter 10 may be used in a variety of vascular procedures, a specific use of the multi-path catheter 10 may include the extracorporeal treatment of bodily fluids. The multi-path catheter 10 may generally include an elongate tubular member 12 having a proximal end 14 and a distal end 16. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular member 12 defines, at least partially, a withdrawal pathway 18 along which unfiltered, or untreated, fluid is withdrawn in the distal to proximal direction, represented by direction arrow $D_1$. The withdrawal pathway 18 originates at a distal point 20 and terminates at the proximal end 14 of the multi-path catheter 10. As should be appreciated, the proximal end 14 of the multi-path catheter 10 may also represent a proximal end of the elongate tubular member 12. The elongate tubular member 12 also defines, at least partially, at least one infusion pathway. According to the exemplary embodiment of FIG. 1, the elongate tubular member 12 defines first and second infusion pathways 22 and 24 along which filtered, or treated, fluid is returned in the proximal to distal direction, which is represented by direction arrow $D_2$. As shown, the first and second infusion pathways 22 and 24 extend distally beyond the withdrawal pathway 18 and are positioned on opposing sides 26 and 28 of the withdrawal pathway 18, particularly at the distal point 20. According to a preferred embodiment, a distance from the distal point 20 of the withdrawal pathway 18 to a distal point of at least one of the infusion pathways 22 and 24, such as, for example, one of distal points 23 and 25, is between about 1 centimeter to about 5 centimeters. More preferably, the distance is between about 2.5 centimeters to about 3 centimeters.

The first and second infusion pathways 22 and 24 may terminate in separate infusion lumens 40 and 42, as shown in the cross sectional view of FIG. 2. The separate infusion lumens 40 and 42 have respective outer walls 44 and 46 that are unattached to one another, as shown in FIGS. 1 and 2. Alternatively, however, and according to embodiments utilizing only one infusion pathway, only one infusion lumen may be provided. As such, tubular member 12 may be characterized as having first and second legs 47 and 48 extending distally therefrom. If only one infusion pathway is provided, only one of the first and second legs 47 and 48 may include an infusion lumen while the other may be solid, as shown in FIGS. 3-5. In either case, the first and second legs 47 and 48, which may have differing lengths as shown in FIG. 3, include the outer walls 44 and 46 that are unattached to one another at distal ends thereof. An alternative cross section to minimize solid leg 48 and maximize the infusion lumen 40 and a withdrawal lumen 49 is shown generally in FIG. 5.

As used herein, "unattached" means that components, such as outer walls 44 and 46, are not joined, connected, or otherwise bound together. As shown in FIGS. 1 and 3, the outer walls 44 and 46 may be unattached from the distal point 20 of the withdrawal pathway 18 through the distal end 16 of the multi-path catheter 10, or from any point along the length of the multi-path catheter 10, as long as the outer walls 44 and 46 are unattached at the distal end 16. As should be appreciated, the outer walls 44 and 46 may be attached, or merged, proximal to the distal point 20. In the cross sectional view of FIG. 2, the separate infusion lumens 40 and 42 are each shown as having a generally round profile. However, those skilled in the art should appreciate that other profiles, such as, for example, oval or D-shaped profiles, may be also be used. Similarly, the single lumen 40 of FIGS. 4 and 5 may have any desired profile.

Turning now to FIG. 6, a specific embodiment, according to the present disclosure, of a multi-path catheter is shown at 50. The multi-path catheter 50, which may, for example, be similar to the partial multi-path catheter 10 of FIG. 1, has a proximal end 52 and a distal end 54 and generally includes an elongate tubular member 56. The proximal end 52, according to the present disclosure, may include a trifurcated fitting, such as a manifold 58. Flexible extension tubes 60, 62, and 64 may extend in the proximal direction from the manifold 58 and may each be in fluid communication with a separate fluid lumen, discussed in greater detail below. Clamps 66, 68, and 70 may be provided for selectively closing off fluid flow through the respective extension tubes 60, 62, and 64, while connecting devices 72, 74, and 76 may be provided for engagement with a treatment device, such as a dialysis machine (not shown).

The multi-path catheter 50 may also include a withdrawal lumen 80, shown in the cross sectional view of FIG. 7, that defines a withdrawal pathway 81, shown in FIG. 6. The withdrawal lumen 80 may originate at a distal point 82 of the withdrawal pathway 81 and may extend in the proximal direction toward the trifurcated manifold 58. According to one embodiment, the withdrawal lumen 80 may extend through the manifold 58 and may be in fluid communication with the extension tube 60. The withdrawal lumen 80 may also include an open distal withdrawal tip 84 that defines a distal withdrawal port 86. During use of the multi-path catheter 50, for example, a bodily fluid, such as blood, may be withdrawn from a patient through the distal withdrawal port 86 of the withdrawal lumen 80.

The multi-path catheter 50 may also include a first infusion lumen 88, shown in the cross sectional views of FIGS. 7 and 8, defining a first infusion pathway 89, and a second infusion lumen 90, also shown in FIGS. 7 and 8, defining a second infusion pathway 91. The first infusion lumen 88 may extend through the manifold 58 and may be in fluid communication with the extension tube 62, while the second infusion lumen 90 may extend through the manifold 58 and may be in fluid communication with the extension tube 64.

As shown, the withdrawal lumen 80, the first infusion lumen 88, and the second infusion lumen 90 may have merged outer walls 92 from the proximal end 52 of the multi-path catheter 50, which may represent a proximal end of the withdrawal lumen 80, to the distal withdrawal port 86. As used herein, "merged" may have a meaning that is opposite of "unattached," and, specifically, may refer to components that are joined, connected, or otherwise bound together. The first and second infusion lumens 88 and 90 or, more particularly, the portions of first and second infusion lumens 88 and 90 extending distally beyond the distal withdrawal port 86 may have unattached outer walls 94 and 96, as shown in the cross sectional view of FIG. 8. Although the first and second infusion lumens 88 and 90 are shown as having oval profiles, it should be appreciated that alternative profiles may also be used according to the present disclosure. For example, as shown in the alternative cross sectional view of FIG. 9, distal portions of first and second infusion lumens 97 and 98 may have round profiles defined by unattached outer walls 99 and 100. Yet alternatively, distal portions of first and second infusion lumens 101 and 102, and withdrawal lumen 105, may have shapes as shown in FIG. 10.

The first and second infusion lumens 88 and 90 may each include an open distal infusion tip 106 and 108 defining a distal infusion port 110 and 112. During use of the multi-path catheter 50, for example, a treated bodily fluid, such as cleansed or filtered blood, may be returned to a patient vessel through the distal infusion ports 110 and 112 of the first and second infusion lumens 88 and 90. Alternatively, or additionally, one or both of the first and second infusion lumens 88 and 90 may include at least one side port 114 defining a distal infusion port 116.

Another embodiment of a multi-path catheter, according to the present disclosure, is shown generally at 120 in FIG. 11. The multi-path catheter 120 has a proximal end 122 and a distal end 124, and generally includes an elongate tubular member 126. The proximal end 122, according to the present disclosure, may include a bifurcated fitting, such as a manifold 128. Flexible extension tubes 130 and 132 may extend in the proximal direction from the manifold 128 and may each be in fluid communication with a separate fluid lumen, as will be discussed below. Clamps 134 and 136 may be provided for selectively closing off fluid flow through the respective extension tubes 130 and 132, while connecting devices 138 and 140 may be provided for engagement with a treatment device, such as, for example, a dialysis machine.

The multi-path catheter 120 may also include a withdrawal lumen 142, shown in the cross sectional views of FIGS. 12-15, that defines a withdrawal pathway 143. The withdrawal lumen 142 may originate at a distal point 144 of the withdrawal pathway 143 and may extend in the proximal direction toward the bifurcated manifold 128. According to one embodiment, the withdrawal lumen 142 may extend through the manifold 128 and may be in fluid communication with the extension tube 130. The withdrawal lumen 142 may also include an open distal withdrawal tip 146 that defines a distal withdrawal port 148. During use of the multi-path catheter 120, a bodily fluid, such as blood, may be withdrawn from a patient through the distal withdrawal port 148 of the withdrawal lumen 142.

The multi-path catheter 120 may also include a dual path infusion lumen 150, shown in FIGS. 12-14, that defines first segments 152 and 154 of first and second infusion pathways 153 and 155. As shown in FIG. 15, the dual path infusion lumen 150 may ultimately branch into separate infusion lumens 156 and 158. The separate infusion lumens 156 and 158 define second segments 160 and 162 of the first and second infusion pathways 153 and 155. According to the exemplary embodiment, merged outer walls 163 of the dual path infusion lumen 150 and the withdrawal lumen 142 may be attached to one another, or merged, from the proximal end 122 of the multi-path catheter 120 to the distal withdrawal port 148. The separate infusion lumens 156 and 158 or, more particularly, the portions of the separate infusion lumens 156 and 158 extending distally beyond the distal withdrawal port 148 may have separate, or unattached, outer walls 165 and 167, as described above with reference to the embodiment of FIG. 6.

As shown in the cross sectional views of FIGS. 12-15, a transition from two lumens (i.e., the withdrawal lumen 142 and the dual path infusion lumen 150) to three lumens (i.e., the withdrawal lumen 142 and the separate infusion lumens 156 and 158) may occur gradually along the length of the multi-path catheter 120. Alternatively, however, the transition may occur at any position along the catheter length. According to one alternative embodiment, for example, the transition from two lumens to three lumens, as described above, may occur within the manifold 128. Although specific profiles are shown for each of the withdrawal lumen 142, dual path infusion lumen 150, and separate infusion lumens 156 and 158, it should be appreciated that alternative profiles are also contemplated herein.

Referring again to FIG. 11, the separate infusion lumens 156 and 158 may each include an open distal infusion tip 164 and 166 defining a distal infusion port 168 and 170. During use of the multi-path catheter 120, for example, a treated bodily fluid, such as cleansed or filtered blood, may be returned to a patient vessel through the distal infusion ports 168 and 170. Alternatively, or additionally, one or both of the separate infusion lumens 156 and 158 may be in fluid communication with at least one side port 172 defining a distal infusion port 174.

Turning now to FIG. 16, the multi-path catheter 120 is shown including an additional feature of the present disclosure. As detailed above, separate infusion lumens, such as infusion lumens 156 and 158 of FIG. 15, may extend at least from the distal withdrawal port 148 to distal points 176 and 178 of the first and second infusion pathways 153 and 155 and may include unattached outer walls 165 and 167. A withdrawal region 180 may extend distally beyond the distal withdrawal port 148 and may include segments of the separate infusion lumens 156 and 158 adjacent the distal withdrawal port 148. A collapse inhibiting member 182 may be attached to outer walls 165 and 167 of the separate infusion lumens 156 and 158 within the withdrawal region 180. The collapse inhibiting member 182, which may be made from plastic or other suitable material, may help inhibit collapse of the outer walls 165 and 167. Although a collapse inhibiting member 182 may be used within the withdrawal region 180, it is not contemplated that such a member be positioned at distal points 176 and 178 of the separate infusion lumens 156 and 158 so as to form a loop. As such, a relatively low profile of the multi-path catheter 120 may be maintained, particularly relative to a catheter incorporating a loop-like structure, which may ease positioning and use of the multi-path catheter 120.

As an alternative to the collapse inhibiting member 182, or in addition to the collapse inhibiting member 182, the multi-path catheter 120 may include marker bands (not shown) that may be bonded on both outer walls 165 and 167. The marker bands may be magnetic and, more specifically, may be opposite in polarity sufficient to repel one another and inhibit collapse of the outer walls 165 and 167. As yet another alternative, an increase in stiffness of the outer walls 165 and 167 within or near the withdrawal region 180 may be provided to reduce or inhibit collapse. Such a collapse, as should be appreciated, may block, or occlude, the distal withdrawal port 148 of the withdrawal lumen 142.

The multi-path catheters described herein may be made from any common catheter material, such as, for example, a plastic, rubber, silicone, or Teflon material, and may be formed using any known catheter forming techniques. For example, a multi-lumen catheter may be made using common catheter forming techniques, such as, for example, by utilizing steel mandrels to form each of the lumens. Thereafter, portions of wall surrounding the withdrawal lumen may be removed, such as by using laser cutting, to form a distal withdrawal port and allow separate infusion lumens, or a single infusion lumen, to extend distally beyond the distal withdrawal port. Alternatively, for example, separate single lumen catheters may be bonded to another single lumen catheter such that distal portions of two of the single lumen catheters, or infusion lumens, extend beyond a distal tip of the other single lumen catheter, or withdrawal lumen. For embodiments utilizing one infusion lumen, a single lumen catheter and a strip of catheter material may be bonded to another single lumen catheter, with distal portions of the infusion lumen catheter and strip of catheter material extend distally beyond a distal tip of the withdrawal lumen. Yet alternatively, separate lumens may be bonded to a distal end of a multi-lumen catheter such that the separate lumens are fluidly connected to infusion lumens positioned on opposing sides of a withdrawal lumen. In all cases, the elongate tubular member will include first and second distally extending legs, whether or not each of the legs includes an infusion lumen. As should be appreciated, a variety of manufacturing methods are contemplated for making a multi-path catheter having the features disclosed herein.

INDUSTRIAL APPLICABILITY

The present disclosure is generally applicable to multi-path catheters for use in vascular procedures. More specifically, the present disclosure finds application in procedures that involve the extracorporeal treatment of bodily fluids. Further, the present disclosure finds specific application in hemodialysis procedures on patients with acute and/or chronic renal failure. Such multi-path catheters may be used for temporary vascular access, while a permanent access develops, or for long-term access, in situations where a permanent access may not be feasible.

Referring generally to FIGS. 1-16 and, more specifically, to the embodiment of FIG. 1, a multi-path catheter 10 may generally include an elongate tubular member 12 having a proximal end 14 and a distal end 16. The elongate tubular member 12 defines, at least partially, a withdrawal pathway 18 along which unfiltered fluid is withdrawn in the distal to proximal direction $D_1$. The elongate tubular member 12 also defines, at least partially, first and second infusion pathways 22 and 24 along which filtered fluid is returned in the proximal to distal direction $D_2$. As shown, the first and second infusion pathways 22 and 24 extend distally beyond the withdrawal pathway 18 and are positioned on opposing sides 26 and 28 of the withdrawal pathway 18, particularly at a distal point 20 of the withdrawal pathway 18. The first and second infusion pathways 22 and 24 terminate in separate infusion lumens 40 and 42 having outer walls 44 and 46 that are unattached to one another, as shown in FIG. 2. The elongate tubular member 12 may be characterized as having first and second legs 47 and 48 extending distally therefrom, wherein the first and second legs 47 and 48 have outer walls 44 and 46 that are unattached to one another at distal ends thereof. According to alternative embodiments, as described above, only one of the first and second legs 47 and 48 may define an infusion lumen, while the other may be solid, as shown in FIGS. 3-5.

A method of performing a hemodialysis procedure on a patient using the catheter disclosed herein will be discussed with general reference to FIG. 17 and specific reference to the embodiments of FIG. 6 and FIG. 11. Initially, the multi-path catheter 50 (FIG. 6) or 120 (FIG. 11) may be inserted into a vessel V, such as the jugular vein, subclavian vein, or the femoral vein, of a patient P over a wire guide (not shown), e.g., via the well known Seldinger percutaneous entry technique. According to the embodiment of FIG. 6, blood may be withdrawn, or aspirated, from the vessel V of the patient P through a distal withdrawal port 86 and passed to a dialysis machine 190, such as a dialyzer. Specifically, unfiltered blood may be withdrawn from the vessel V of the patient P in the distal to proximal direction $D_1$ through a withdrawal lumen 80. The unfiltered blood may be passed through the dialysis machine 190, where waste products are removed from the blood. The treated blood from the dialysis machine 190 may then be returned to the patient vessel V. Specifically, the filtered blood may be directed into a vessel V of the patient P in the proximal to distal direction $D_2$ through first and second infusion lumens 88 and 90, also referred to as separate infusion lumens. The filtered blood may be directed from the first and second infusion lumens 88 and 90 through open distal infusion tips 106 and 108 and/or side port 114.

According to the embodiment of FIG. 11, blood may be withdrawn from the patient vessel V through a distal withdrawal port 148 and passed to the dialysis machine 190. Specifically, unfiltered blood may be withdrawn from the vessel V of the patient P in the distal to proximal direction $D_1$ through a withdrawal lumen 142. As stated above, the dialysis machine 190 may remove wastes from the blood before returning the blood to the patient P. The filtered fluid may be returned to the vessel V of the patient P in the proximal to distal direction $D_2$ by first directing the filtered blood through a dual path infusion lumen 150 and next branching the filtered blood to separate infusion lumens 156 and 158. The filtered blood may be directed through open distal infusion tips 164 and 166 and/or side port 172 of the separate infusion lumens 156 and 158.

In all of the embodiments contemplated herein, the distal withdrawal port 86 (FIG. 6) or 148 (FIG. 11) is positioned proximal to infusion ports 110, 112, and 116 (FIG. 6) or 168, 170, and 174 (FIG. 11), which may include any combination of open distal infusion tips and/or side ports. Specifically, distal points, such as distal points 176 and 178 shown in FIG. 16, of the first and second infusion pathways 153 and 155 (FIGS. 11 and 16) may be positioned a predetermined distance from the distal point 82 or 144 of the respective withdrawal pathways 81 (FIG. 6) or 143 (FIGS. 11 and 16). Such positioning may serve to inhibit fluid recirculation or, more specifically, ensure that a majority of the blood that is aspirated through the distal withdrawal ports 86 (FIG. 6) or 148 (FIG. 11) is not the same blood that has been treated and returned to the patient vessel V.

Also, in the embodiments contemplated herein, the distal point 82 or 144 of the respective withdrawal pathway 81 (FIG. 6) or 143 (FIGS. 11 and 16) is flanked with the first and second infusion pathways 89 and 91 (FIG. 6) or 153 and 155 (FIGS. 11 and 16). This serves to inhibit blockage of the withdrawal pathway 81 (FIG. 6) or 143 (FIGS. 11 and 16), which may occur if the distal withdrawal port 86 (FIG. 6) or 148 (FIG. 11) of the withdrawal lumen 80 (FIG. 6) or 142 (FIGS. 11 and 16) suctions against the vessel wall. Specifically, the outer walls 94 and 96 (FIG. 6) or 165 and 167 (FIG. 11) of the separate infusion lumens 88 and 90 (FIG. 6) or 156 and 158 (FIG. 11) may block the distal withdrawal port 86 (FIG. 6) or 148 (FIG. 11) by "sucking" against the vessel wall and leaving the withdrawal lumen 80 (FIG. 6) or 142 (FIG. 11) partially or completely occluded. Such occlusion, as should be appreciated, may have catastrophic effects on the hemodialysis, or other, procedure being performed.

In addition, outer walls 94 and 96 (FIG. 6) or 165 and 167 (FIG. 11) of the separate infusion lumens 88 and 90 (FIG. 6) or 156 and 158 (FIG. 11) may be urged away from one another using a collapse inhibiting member 182 (FIG. 16), described above. This may serve to inhibit collapse of the separate infusion lumens 88 and 90 (FIG. 6) or 156 and 158 (FIG. 11) onto the distal withdrawal port 86 (FIG. 6) or 148 (FIG. 11), which may ultimately block the withdrawal lumen 80 (FIG.

6) or 142 (FIGS. 11 and 16). Alternative means for inhibiting such collapse may include increasing a stiffness of the catheter at or near the distal withdrawal port 86 (FIG. 6) or 148 (FIG. 11), or utilizing alternative components that may serve to urge the outer walls 94 and 96 (FIG. 6) or 165 and 167 (FIG. 11) of the separate infusion lumens 88 and 90 (FIG. 6) or 156 and 158 (FIG. 11) away from one another.

If the catheter described herein is to remain within the patient for a later treatment, it may be desirable to inject a heparin lock solution into the catheter. According to some of the embodiments disclosed herein, particularly the embodiment of FIG. 6, each of the separate lumens 88 and 90 (FIG. 6) may be independently locked using a well known heparin lock solution. As shown in FIG. 17, for example, a heparin lock solution may be injected into separate lumens 192 using one or more syringes 194. If such independent control is desired, the embodiment of FIG. 11 may be modified such that the transition from two lumens (i.e., the withdrawal lumen 142 and the dual path infusion lumen 150) to three lumens (i.e., the withdrawal lumen 142 and the separate infusion lumens 156 and 158) occurs at the proximal end 122 of the catheter, such as, for example, within the manifold 128, or other at another location that is accessible by the clinician. As should be appreciated, such independent control may provide assurance to the clinician that each lumen is sufficiently locked until the next procedure.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A multi-path catheter, including:
   an elongate tubular member;
   a withdrawal pathway along which unfiltered fluid is withdrawn in a distal to proximal direction, wherein the withdrawal pathway is at least partially defined by the elongate tubular member and originates at a port located at a distal point in the elongate tubular member; and
   at least one infusion pathway along which filtered fluid is returned in a proximal to distal direction, wherein the at least one infusion pathway extends distally beyond the withdrawal pathway and is at least partially defined by the elongate tubular member;
   wherein the elongate tubular member includes first and second legs positioned on opposing sides of, and being separated by a width of, the withdrawal pathway at the distal point so that the first and second legs are noncontiguous to each other at the distal point, and wherein the at least one infusion pathway is at least partially defined by one of the first and second legs;
   wherein the first and second legs have outer walls that are unattached to one another at distal ends thereof such that a clearance between the first and second legs extends in a distal direction from the port.

2. The multi-path catheter of claim 1, further including first and second infusion pathways extending distally beyond the withdrawal pathway, wherein the first infusion pathway is at least partially defined by the first leg and the second infusion pathway is at least partially defined by the second leg, wherein the first and second infusion pathways terminate in separate infusion lumens.

3. The multi-path catheter of claim 2, further including a withdrawal lumen defining the withdrawal pathway.

4. The multi-path catheter of claim 3, further including a first infusion lumen defining the first infusion pathway, and a second infusion lumen defining the second infusion pathway.

5. The multi-path catheter of claim 4, wherein outer walls of the first infusion lumen, the second infusion lumen and the withdrawal lumen are attached to one another from a proximal end of the withdrawal lumen to the distal withdrawal port.

6. The multi-path catheter of claim 5, wherein the first and second infusion lumens each include an open distal infusion tip defining a distal infusion port.

7. The multi-path catheter of claim 3, further including a dual path infusion lumen defining first segments of the first and second infusion pathways, wherein the dual path infusion lumen branches into the separate infusion lumens, wherein the separate infusion lumens define second segments of the first and second infusion pathways.

8. The multi-path catheter of claim 7, wherein outer walls of the dual path infusion lumen and the withdrawal lumen are attached to one another from a proximal end of the withdrawal lumen to the distal withdrawal port.

9. The multi-path catheter of claim 8, wherein the separate infusion lumens each include an open distal infusion tip defining a distal infusion port.

10. The multi-path catheter of claim 3, wherein the separate infusion lumens extend at least from the distal withdrawal port to distal points of the first and second infusion pathways.

11. The multi-path catheter of claim 10, further including a withdrawal region extending distally beyond the distal withdrawal port and including segments of the separate infusion lumens adjacent the distal withdrawal port, wherein a collapse inhibiting member is attached to the outer walls of the separate infusion lumens within the withdrawal region.

12. The multi-path catheter of claim 1, wherein a distance from the distal point of the withdrawal pathway to a distal point of the at least one infusion pathway is between about 2.5 centimeters to about 3 centimeters.

13. A method of performing a hemodialysis procedure on a patient using a multi-path catheter, the multi-path catheter including an elongate tubular member, a withdrawal pathway along which unfiltered fluid is withdrawn in a distal to proximal direction, wherein the withdrawal pathway originates at a distal point and is at least partially defined by the elongate tubular member, at least one infusion pathway along which filtered fluid is returned in a proximal to distal direction, wherein the at least one infusion pathway extends distally beyond the withdrawal pathway and is at least partially defined by the elongate tubular member, wherein the elongate tubular member includes first and second legs positioned on opposing sides of the withdrawal pathway at the distal point, wherein the at least one infusion pathway is at least partially defined by one of the first and second legs, wherein the first and second legs have outer walls that are unattached to one another at distal ends thereof, the method including the steps of:
   directing the filtered fluid into a vessel of the patient through at least one infusion lumen, wherein the at least one infusion lumen is at least partially defined by one of the first and second legs;
   inhibiting blockage of the withdrawal pathway, at least in part, by the first and second legs, wherein the first and second legs are noncontiguous with each other at the distal point and positioned so as to flank, and be separated by a width of, the withdrawal pathway at the distal point and define a clearance extending in a distal direction from a port opening of the withdrawal pathway and located at the distal point; and inhibiting fluid recirculation, at least in part, by spacing a distal point of the at least one infusion pathway a predetermined distance from the distal point of the withdrawal pathway.

14. The method of claim 13, wherein the directing step includes directing the filtered fluid into the vessel of the patient along first and second infusion pathways, wherein the first and second infusion pathways terminate in separate infusion lumens.

15. The method of claim 14, further including withdrawing the unfiltered fluid from the vessel of the patient in the distal to proximal direction through a withdrawal lumen.

16. The method of claim 15, further including returning the filtered fluid to the vessel of the patient in the proximal to distal direction through first and second infusion lumens.

17. The method of claim 15, further including returning the filtered fluid to the vessel of the patient in the proximal to distal direction by first directing the filtered fluid through a dual path infusion lumen and next branching the filtered fluid to the separate infusion lumens.

18. The method of claim 15, further including directing the filtered fluid through open distal infusion tips of the separate infusion lumens.

19. The method of claim 14, wherein the step of inhibiting blockage of the withdrawal pathway includes urging the outer walls of the separate infusion lumens away from one another using a collapse inhibiting member.

20. The method of claim 14, further including independently locking the separate infusion lumens using a heparin lock solution.

* * * * *